United States Patent [19]

Warriner

[11] Plant 4,851

[45] May 25, 1982

[54] ROSE PLANT 75-3831

[75] Inventor: William A. Warriner, Tustin, Calif.

[73] Assignee: Jackson & Perkins Company, Medford, Oreg.

[21] Appl. No.: 190,092

[22] Filed: Sep. 23, 1980

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh, Whinston & Dellett

[57] ABSTRACT

A hybrid tea variety having red flowers, on long to medium stems, very mildew resistant foliage and very little fragrance.

1 Drawing Figure

1

This present invention relates to a new and distinct variety of rose plant of the hybrid tea class which was originated by me by crossing an unnamed variety with the variety Samantha, U.S. Plant Pat. No. 3,727.

The primary objective of this breeding was to produce a new rose variety combining the non-fading red flower color of Samantha with flower form and disease resistance of the unnamed variety. This objective was substantially achieved along with other desirable improvements as evidenced by the following unique combination of characteristics which are outstanding in the new variety and which distinguish it from its parents as well as from all other varieties of which I am aware:

1. Very mildew resistant foliage.
2. Larger foliage than Samantha when grown in same environment.
3. Flowers at 20 to 25 petals which at maturity are more quilled than those of Samantha.
4. New foliage much lighter color than that of Samantha.
5. Red flower color very near that of Samantha, but with fewer white streaks on outer petals.
6. Very little fragrance.
7. Particularly suitable as a variety to be grown in greenhouses for production of cut blooms.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Unnamed variety.

*Pollen parent.*—Samantha, U.S. Plant Pat. No. 3,727.

Classification:

*Botanical.*—Rosa hybrid.

*Commercial.*—Hybrid tea.

2

FLOWER

Observations made from specimens grown in a greenhouse at Irvine, Calif., in August, 1980.

Blooming habit: Continuous.

Bud:

*Size.*—$1\frac{1}{2}''$ when petals start to unfurl.

*Form.*—Pointed ovoid, broad base.

*Color.*—When sepals first divide, near Red 47A, overlayed where first exposed with Red-Purple 183B. When half blown, upper side of petals near 45A, lower side of petals near Red 53C.

*Sepals.*—Color: Outer surface, Green 138B. Surface nearly smooth, having a few stipitate glands. Three appendaged sepals, lightly appendaged. Two unappendaged sepals hairy edged.

*Receptacle.*—Color: Green 138B. Shape: Funnel. Size: Large. Surface: Smooth.

*Peduncle.*—Length: Long. Surface: Prickle, with very small prickles. Color: Light green. Strength: Stiff, slender.

*Opening.*—Outer petals fold outward and tips curl back.

Bloom:

*Size.*—Large. Average open size is 4'' to $4\frac{1}{2}''$.

*Borne.*—Single, or several together.

*Stems.*—Long to medium, normal strength.

*Form.*—When first open, high centered. Permanence: Outer petals edges slightly curled and pointed.

*Petalage.*—Number of petals under normal conditions 20 to 25.

*Color.*—Center of flower: Upper side of petals near Red 45A; reverse side of petals near Red 53C; base of petals very small white area at point of attachment. General tonality from a distance, Red 45A.

*Variegations.*—Rarely a white streak at midrib of outer petals.

*Discoloration.*—General tonality at third day, no change, Red 45A.

*Fragrance.*—Very slight.

Petals:

*Texture.*—Thick.

*Shape.*—Round, to wider than long.

*Form.*—Edges slightly quilled.

*Arrangement.*—Loosely imbricated. Petaloids in center, few.

*Persistence.*—Drop off cleanly.

*Lastingness.*—On the plant, very long. As cut flower, very long.

*Anthers.*—Medium, many. Color: Yellow. Arrangement, regular around styles.

*Filaments.*—Color: White.

*Pollen.*—Gold yellow.

*Styles.*—Color: Red.

*Stigmas.*—Color: White.

PLANT

Form: Bush.

Growth: Very vigorous.

Foliage: Number of leaflets on normal mid-stem leaves, 5 or 7.

*Size.*—Large.

*Quantity.*—Normal.

*Color.*—New foliage: Light green, heavily shaded or overlayed with pigment near Greyed Purple 183D. Old foliage, Green 137A.

Leaflets:

*Shape.*—Oval pointed.

*Texture.*—Upper side: Leathery.

*Edge.*—Serrated.

*Serration.*—Single, small.

*Petiole.*—Rachis: Color: Reddish. Underside: Prickles.

*Stipules.*—Long, bearded.

*Disease resistance.*—Very resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalks, ordinary.

*Form.*—Long base, hooked slightly downward.

*Color when young.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of light colored new growth, mildew resistant foliage, red flowers with 20 to 25 petals and very little fragrance, particularly suitable for the production of cut blooms in greenhouses.

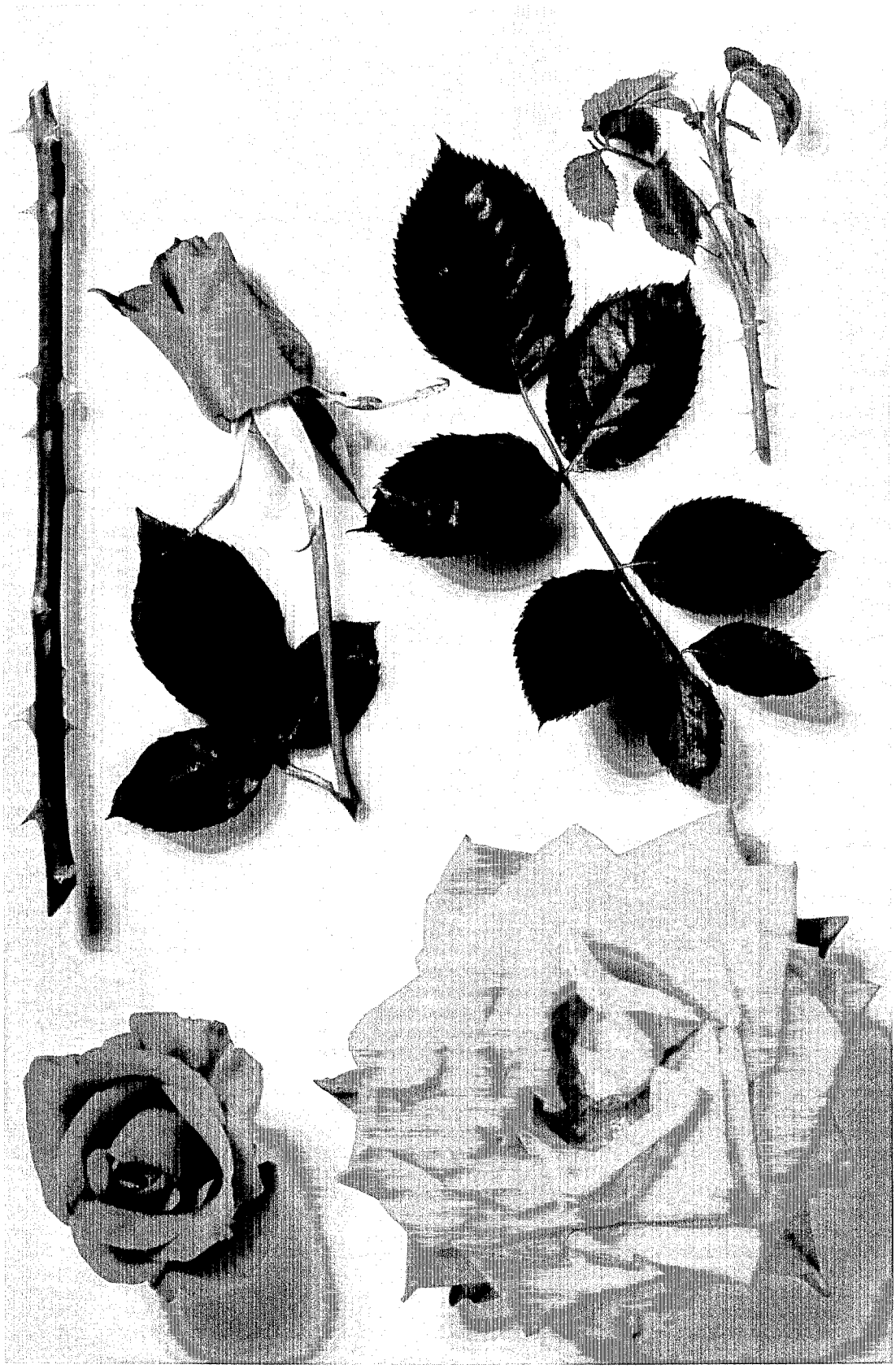

* * * * *